(12) United States Patent
Kay et al.

(10) Patent No.: US 12,150,681 B2
(45) Date of Patent: *Nov. 26, 2024

(54) INTRAMEDULLARY IMPLANT WITH PROXIMAL PLATE AND METHOD FOR ITS USE

(71) Applicant: WRIGHT MEDICAL TECHNOLOGY, INC., Memphis, TN (US)

(72) Inventors: David B. Kay, Akron, OH (US); Anthony Perera, Cardiff (GB); Bryan Den Hartog, St. Paul, MN (US); Dustin Ducharme, Stow, OH (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 63 days.

This patent is subject to a terminal disclaimer.

(21) Appl. No.: 18/163,927

(22) Filed: Feb. 3, 2023

(65) Prior Publication Data

US 2023/0172645 A1 Jun. 8, 2023

Related U.S. Application Data

(63) Continuation of application No. 16/869,716, filed on May 8, 2020, now Pat. No. 11,596,457, which is a
(Continued)

(51) Int. Cl.
*A61B 17/72* (2006.01)
*A61B 17/17* (2006.01)
(Continued)

(52) U.S. Cl.
CPC ...... *A61B 17/7291* (2013.01); *A61B 17/1717* (2013.01); *A61B 17/68* (2013.01);
(Continued)

(58) Field of Classification Search
CPC ... A61B 17/7291; A61B 17/72; A61B 17/746; A61B 17/7233
See application file for complete search history.

(56) References Cited

U.S. PATENT DOCUMENTS

| 6,203,545 B1 | 3/2001 | Stofella |
|---|---|---|
| 6,248,109 B1 | 6/2001 | Stofella |

(Continued)

FOREIGN PATENT DOCUMENTS

| CN | 204655083 U | 9/2015 |
|---|---|---|
| DE | 202008010922 U | 7/2010 |

(Continued)

OTHER PUBLICATIONS

Extended European Search Report in connection with corresponding Patent Application No. 17851594.6, Feb. 18, 2020, 7 pages.
(Continued)

*Primary Examiner* — Andrew Yang
(74) *Attorney, Agent, or Firm* — DUANE MORRIS LLP

(57) ABSTRACT

An orthopedic implant is specifically configured for use in osteotomies, in which part of the implant extends into an intramedullary portion of a first bone segment and a plate portion is external to the cortical surface of an adjacent bone segment to fix the segments to allow them to fuse. The body of the implant has a first end and a second end where the end which is inserted into the bone has a chamfer and a through hole having a hole axis optionally at an oblique angle to the longitudinal axis of the implant, and which can receive a screw, peg or pin. The second end of the implant includes a plate portion with at least two offset screws.

17 Claims, 3 Drawing Sheets

Related U.S. Application Data continuation of application No. 15/704,195, filed on Sep. 14, 2017, now Pat. No. 10,682,168.

(60) Provisional application No. 62/394,928, filed on Sep. 15, 2016.

(51) Int. Cl.
 *A61B 17/68* (2006.01)
 *A61B 17/86* (2006.01)

(52) U.S. Cl.
 CPC .......... *A61B 17/86* (2013.01); *A61B 17/1775* (2016.11); *A61B 17/1782* (2016.11)

(56) References Cited

U.S. PATENT DOCUMENTS

| | | |
|---|---|---|
| 6,355,041 B1 | 3/2002 | Martin |
| 6,689,136 B2 | 2/2004 | Stofella |
| 6,706,046 B2 | 3/2004 | Orbay et al. |
| 6,926,720 B2 | 8/2005 | Castaneda |
| 7,563,263 B2 | 7/2009 | Orbay et al. |
| 7,686,808 B2 | 3/2010 | Orbay et al. |
| 7,727,264 B2 | 6/2010 | Orbay et al. |
| 7,927,341 B2 | 4/2011 | Orbay et al. |
| 7,938,850 B2 | 5/2011 | Orbay et al. |
| 8,083,783 B2 | 12/2011 | Ullman et al. |
| 8,167,918 B2 | 5/2012 | Strnad et al. |
| 8,608,783 B2 | 12/2013 | Graham et al. |
| 8,628,533 B2 | 1/2014 | Graham et al. |
| 8,685,024 B2 | 4/2014 | Roman |
| 8,715,325 B2 | 5/2014 | Weiner et al. |
| 8,753,343 B2 | 6/2014 | Staeubli |
| 8,858,602 B2 | 10/2014 | Weiner et al. |
| 8,888,778 B2 | 11/2014 | Roman |
| 8,926,612 B2 | 1/2015 | Graham |
| 8,998,999 B2 | 4/2015 | Lewis et al. |
| 9,017,329 B2 | 4/2015 | Tyber et al. |
| 9,226,783 B2 | 1/2016 | Brigido |
| 9,452,002 B2 | 9/2016 | Roman et al. |
| 9,486,258 B2 | 11/2016 | Roman et al. |
| 9,554,916 B2 | 1/2017 | Miller |
| 9,597,130 B2 | 3/2017 | Pappalardo et al. |
| 9,615,873 B2 | 4/2017 | Weiner et al. |
| 9,629,671 B2 | 4/2017 | Roman |
| 9,717,543 B2 | 4/2017 | Brown et al. |
| 9,642,656 B2 | 5/2017 | Kotuljac et al. |
| 9,675,391 B2 | 6/2017 | Roman et al. |
| 9,788,871 B2 | 10/2017 | Simon |
| 9,867,642 B2 | 1/2018 | Simon |
| 9,907,562 B2 | 3/2018 | Dacosta et al. |
| 9,943,347 B2 | 4/2018 | Wayne et al. |
| 10,080,597 B2 | 9/2018 | Shemwell et al. |
| 2005/0033302 A1 | 2/2005 | Frank |
| 2006/0149257 A1 | 7/2006 | Orbay |
| 2006/0161156 A1 | 7/2006 | Orbay |
| 2006/0206044 A1 | 9/2006 | Simon |
| 2007/0083202 A1 | 4/2007 | Running et al. |
| 2007/0191855 A1 | 8/2007 | Orbay |
| 2009/0009812 A1 | 1/2009 | Sirringhaus |
| 2009/0036931 A1 | 2/2009 | Pech et al. |
| 2009/0069812 A1 | 3/2009 | Gillard et al. |
| 2009/0118769 A1 | 5/2009 | Sixto, Jr. et al. |
| 2010/0274293 A1 | 10/2010 | Terrill et al. |
| 2011/0106157 A1 | 5/2011 | Melkent et al. |
| 2011/0137313 A1 | 6/2011 | Jensen et al. |
| 2012/0016426 A1 | 1/2012 | Robinson |
| 2013/0066383 A1 | 3/2013 | Anderson et al. |
| 2013/0123862 A1 | 5/2013 | Anderson et al. |
| 2013/0158608 A1 | 6/2013 | Viola et al. |
| 2013/0204250 A1 | 8/2013 | McDevitt et al. |
| 2013/0338722 A1 | 12/2013 | Yaliz |
| 2014/0018812 A1 | 1/2014 | Graham |
| 2014/0074174 A1 | 3/2014 | Schacherer et al. |
| 2014/0107798 A1 | 4/2014 | Jeng et al. |
| 2014/0243837 A1 | 8/2014 | Mebarak |
| 2014/0277178 A1 | 9/2014 | O'Kane et al. |
| 2014/0277532 A1 | 9/2014 | Teeny et al. |
| 2015/0164565 A1 | 6/2015 | Johnson et al. |
| 2016/0051295 A1 | 2/2016 | Nakamura et al. |
| 2016/0074079 A1 | 3/2016 | Leemrijse et al. |
| 2016/0157900 A1 | 6/2016 | Simon |
| 2016/0157902 A1 | 6/2016 | Simon |
| 2016/0199110 A1 | 7/2016 | Austin et al. |
| 2016/0354127 A1 | 12/2016 | Lundquist |

FOREIGN PATENT DOCUMENTS

| | | |
|---|---|---|
| JP | 2015155032 A | 3/2015 |
| JP | 2015044053 A | 8/2015 |
| WO | 2003101320 A1 | 11/2003 |
| WO | 2007109437 A1 | 9/2007 |
| WO | 2011002903 A2 | 1/2011 |

OTHER PUBLICATIONS

First Office Action issued in connection with corresponding Japanese Patent Application No. 2018-199272, Dec. 1, 2019, 6 pages.
Third Examination Report issued in connection with corresponding Australian Patent Application No. 2017325993, Nov. 25, 2019, 6 pages.
Office Action issued in connection with corresponding Canadian Patent Application No. 3,021,444, Oct. 1, 2019, 6 pages.
Second Examination Report issued in connection with Australian Patent Application No. 2017325993, Jul. 11, 2019, 5 pages.
Extended European Search Report issued in connection with European Patent Application No. 18202235.0, Jun. 12, 2019, 10 pages.
First Examination Report issued in connection with Australian Patent Application No. 2018253511, Mar. 4, 2019, 10 pages.
Second Office Action issued in connection with corresponding Japanese Patent Application No. 2018-199272, Mar. 3, 5 pages.
Ortholoc 3DI Crosscheck Plating System, Wright Medical Group, http://www.wrighl.com/footandankleproductsortholoc-3di-crosscheckplating-system, Aug. 17, 2017.
Hallux 360, Wright Medical Group, Apr. 2017.
Second Office Action issued in connection with corresponding Japanese Patent Application No. 2019-514234, Jan. 5, 2021, 6 pages.
Third Office Action issued in connection with corresponding Japanese Patent Application No. 2019-514234, May 5, 2021, 3 pages.

INTRAMEDULLARY IMPLANT WITH PROXIMAL PLATE AND METHOD FOR ITS USE

CROSS-REFERENCE TO RELATED APPLICATIONS

This application is a continuation of U.S. patent application Ser. No. 16/869,716, filed May 8, 2020, which is a continuation of U.S. patent application Ser. No. 15/704,195, filed Sep. 14, 2017 (now U.S. Pat. No. 10,682,168), which claims benefit of provisional U.S. Patent Application No. 62/394,928, filed Sep. 15, 2016, the entireties of which are incorporated herein by reference.

FIELD OF THE INVENTION

The present invention relates to an orthopedic intramedullary implant, which is configured for a minimally invasive procedure for the fixation of a bone or bones of the foot, hand or wrist in particular following a procedure for fusion of adjacent segments or reconstruction such as various osteotomy procedures. The invention also relates to a method for the use of the orthopedic implant and instruments for use with the implant in surgical procedures.

BACKGROUND OF THE INVENTION

There are several conditions, such as hallux valgus, or more commonly "bunions", which result from congenital deformation or which arise as a result of repeated use type injuries. Surgical intervention that includes surgical sectioning of bone or an "osteotomy" is often used to restructure the bones as a treatment for such conditions. For example, the chevron translational osteotomy, of the first metatarsal with which the present invention might be used, is typically used to treat a condition that is the result of adult acquired metatarsal deformity. The present invention is likewise useful for other conditions of the foot or hand that result from prior trauma, surgical intervention or defects from birth or that develop with age (such as rheumatoid arthritis).

Examples of some of the procedures with which the present invention could be used include hallus valgus and hallus rigidus corrections, and bunionectomies. Other applications which could use the present invention include first and fifth metatarsal chevrons, translational osteotomies, closing wedge osteotomies, pediatric femoral osteotomies, metacarpal and calcaneal rotational osteotomies, intraarticular osteotomies and hand and wrist realignment osteotomies.

SUMMARY OF THE INVENTION

In accordance with the present invention an orthopedic intramedullary implant (as well as a surgical method which uses the implant) is provided which can be used to good advantage in an osteotomy. In a first embodiment, the implant has a body having an exterior continuous curved surface formed around a long axis and configured to lodge within the intramedullary channel of the associated bone so as to avoid rotation within the channel. The body preferably has a basic shape (meaning an outline exclusive of the optional flange, striation or groove meant to further stabilize the body in the intramedullary channel) which preferably forms a closed rounded cross-section including a circle or oval which can be the same dimension along the axis or not, to form a three dimensional figure such as a cylindrical, ellipsoid, torpedo, or egg shape. The body portion also has a first end that is tapered or sharpened for insertion, and a longitudinally opposing second end that either cooperates with or extends into a plate portion so as to form an integral substantially exclusive (meaning that the implant has only the body and the plate, and no other arms, or plate members) two member implant that further includes means for fastening to the cortical section of a bone. This first end (of the body member) includes a rounded or tapered chamfered edge such as a counterbore that promotes insertion into the bone. Between the first end and the second end, the implant includes at least one through hole so that the implant can be fixed through an extramedullary portion of a co-axial bone segment. Likewise, the plate portion includes one or more, and preferably two, offset through holes that receive cortical bone screws which are optionally locking bone screws (i.e. including threads on the head which cooperate with internal threads on the through holes of the plate portion).

The invention can be used in a variety of indications including for example, calcaneal osteotomies Dwyer osteotomy, cotton osteotomy, isolated TMT fusion, Navicular fracture, Evans osteotomy and metacarpal rotational osteotomies, or intraarticular osteotomies or hand and wrist realignment osteotomies. Other applications which could use the present invention include first and fifth metatarsal chevrons, translational osteotomies, and closing wedge osteotomies.

DETAILED DESCRIPTION OF THE INVENTION

Figure 1A:
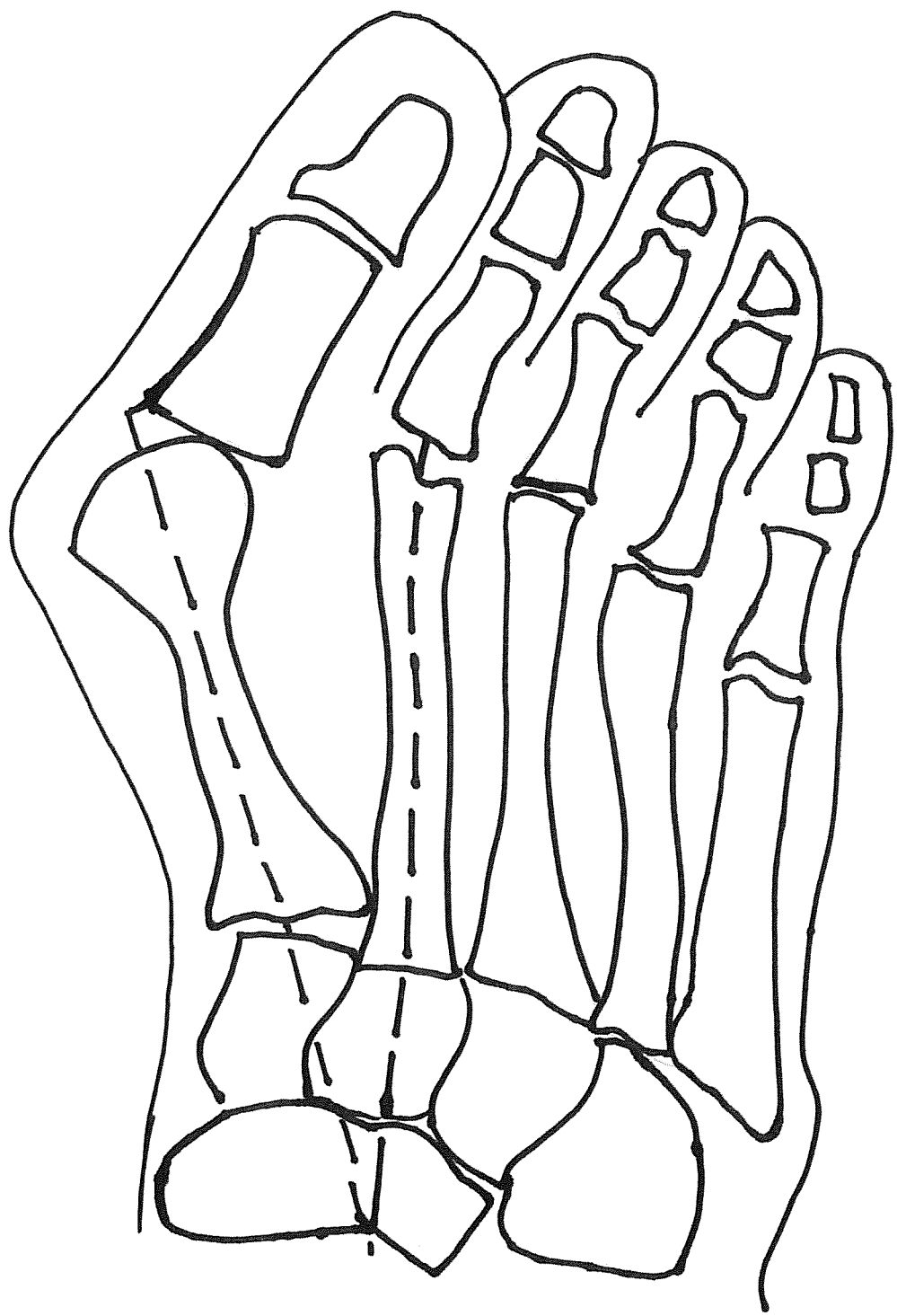
FIG. 1a is posterior view of a foot with a hallux valgus deformity
Figure 1B:
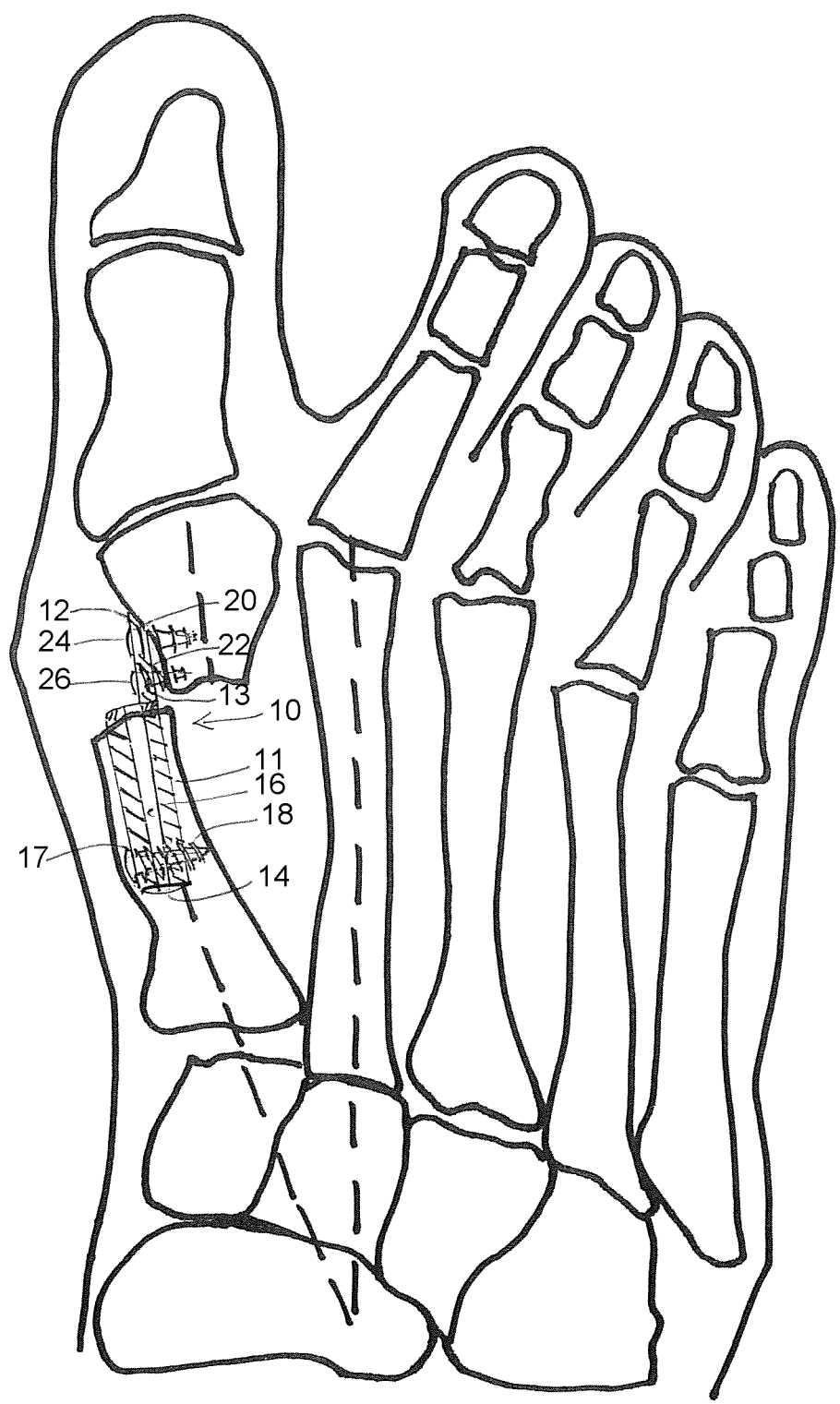
FIG. 1b is a posterior view of a foot with the implant of the present invention following a translational chevron osteotomy procedure.
Figure 2:
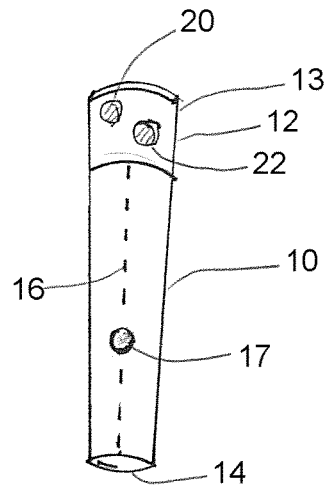
FIG. 2 is a side view of the orthopedic implant of FIG. 1 (b)
Figure 3:
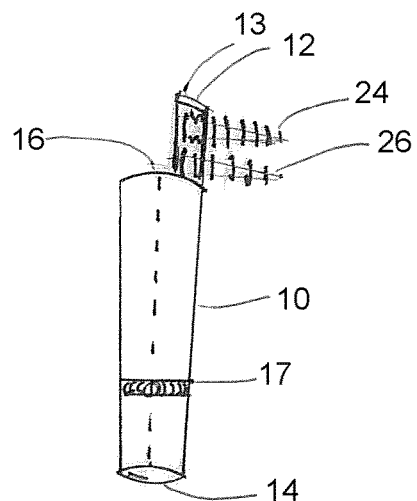
FIG. 3 is a side view of the plate shown in FIG. 2.

FIG. 1 (a) shows a skeletal version of a foot from the top side illustrating a deformity with which the present implant could be used, and FIG. 1 (b) shows the same version of the foot following the method of the present invention with an embodiment of the implant 10 of the present invention in place inserted into the intramedullary channel of the first metatarsal following an osteotomy and the translation of the distal portion of the metatarsal. Thus, FIG. 1 (b) illustrates the implant used in a translational osteotomy of the first metatarsal for treatment of hallux valgus syndrome. Similarly, it can be used for fixation of other bone segments following osteotomies as previously mentioned.

Figure 4:
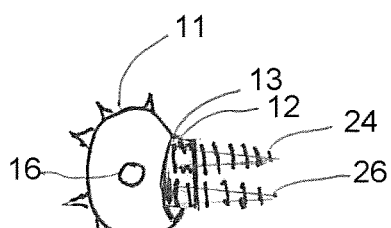
FIG. 4 is an end view of the plate shown in FIG. 3.

As viewed from the top in FIG. 1 (b), it can be seen that the first embodiment of the plate 10 has a body member 11 shaped for insertion into the intramedullary portion of the bone following the osteotomy with a first end 12 that extends into a plate portion 13 and an opposing cutting end 14 aligned along the longitudinal axis of the plate which further includes a cannulation 16 which extends through the body member to allow for the insertion or use of a k-wire. The body of the implant further includes a through hole 17 closer to the second end than the first which again is optionally threaded, for a screw 18 which is optionally a locking screw. The screw is intended to inhibit rotation of the implant in the channel. The body portion is sized and shaped for insertion into the intramedullary channel of a bone, for example, it may be cylindrical or ellipsoid, or have an elongate shape that is relatively round in cross-section but which is less regular than a cylinder or ellipse. The outer surface may be smooth, or may include one or more raised portions 15 (illustrated in FIG. 4), such as grooves, flutes or flanges which extend parallel to the cannulation part of all of the way down the length of the body member or which spiral around the body member) in order to inhibit the implant from rotating within the inner portion of the bone.

The plate portion 13 has a profile when viewed straight on in the widest dimension which is sized to accommodate the specific application, in this case so that it will best conform to the remaining head of the metatarsal, and further includes at least a first through hole 20 (optionally threaded) for a screw 24 (optionally locking) and preferably a second through hole 22 (also optionally threaded) for a second screw 26 (again optionally locking). Specifically, in the illustrated application for a bunionectomy, the plate portion has an outline viewed from the outer surface of a tab or partial egg shape, and the bone facing surface is curved so as to form a section of a cylinder (corresponding to an idealized shape of the head of the associated metatarsal).

Figure 5:
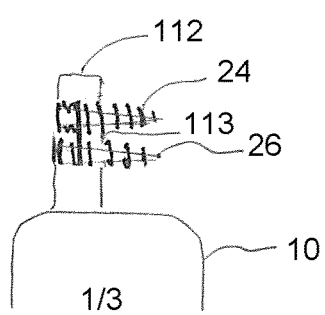
FIG. 5 is a side detail of the plate portion of a second embodiment of the plate shown in FIG. 2.
Figure 6:
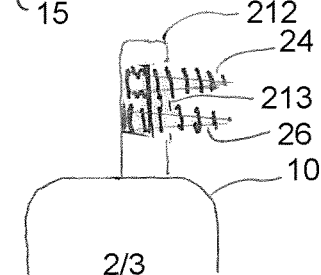
FIG. 6 is a side detail of the plate portion of a third embodiment of the plate shown in FIG. 2
Figure 7:
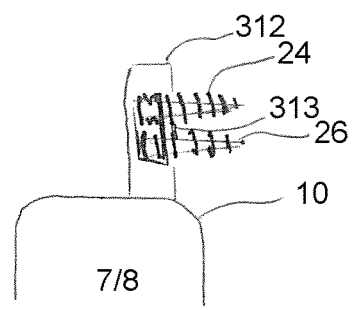
FIG. 7 is a side detail of the plate portion of a fourth embodiment of the plate shown in FIG. 2.
Figure 8:
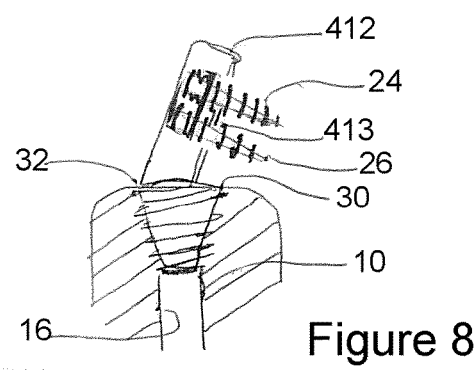
FIG. 8 is a side detail of the plate portion of a fifth embodiment of the plate shown in FIG. 2.

FIGS. 5 through 8 illustrate various embodiments of the implant 10, in which the plate portion is offset to accommodate particular anatomical variations, of ⅓ of the distance across the diameter at the top surface of the implant in FIG. 5, of ⅔ of the distance across the diameter at the top surface of the implant in FIG. 6, and of ⅞ of the distance across the diameter at the top surface of the implant in FIG. 7, and in FIG. 8, the plate portion is angled at from 2° to 15°, and preferably from 7° to 12° relative to the axis of the body member to inhibit a Varus tilt. Further this drawing illustrates the body and plate as an assembly, as compared to the other integrally formed plate and body members. In FIG. 8, the plate portion 413 extends from a threaded tap member 30 that is received in a threaded screw hole 32 in the body member. In this embodiment, various plate portions with varying degrees and/or angles of offset can be used in the body member to simplify the inventory of the system.

Figure 9:
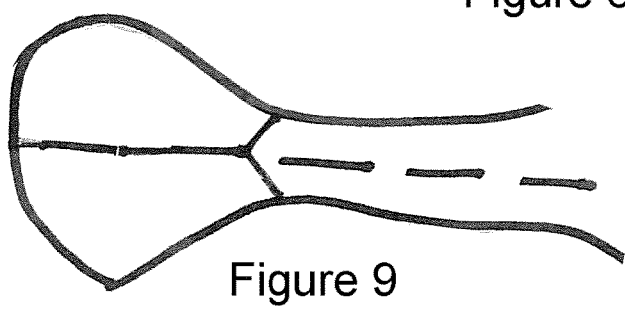
FIG. 9 is a side view of a first metatarsal illustrating the cuts for a method of the present invention.
Figure 10:
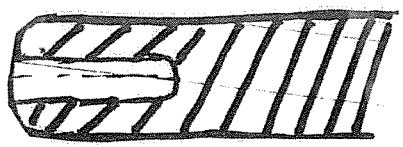
FIG. 10 is a side view of the metatarsal of FIG. 9 following the osteotomy and a counter-bore procedure to prepare for the implant of the present invention.

FIGS. 9 and 10 illustrate steps of the surgical procedure of the present invention where in FIG. 9 multiple incisions are made to the head and at about 1 cm down the neck of the metatarsal. Next, a tool is placed to translate the head of the metatarsal laterally and the remaining proximal portion of the bone is reamed in an Eichhorn shape as is shown in FIG. 10. Next with pushing or drilling, a k-wire is placed in the metatarsal to the base, and the bone is reamed by power or hand. The guide wire is left in place. Then the implant is pushed into position over the guide wire and into the intramedullary channel using a cross-jig which is radiographically located. The screws are inserted into the plate portion, and the implant is pushed into the proximal portion of the bone to compress. The cross screw is inserted, the jigs are disassembled and the guide wire is removed, the medial ledge is removed, including a saw is used or a burr if a mini-incision is used. Graft is added as needed and the incision is closed.

The screws useful with the plate of the present invention are self-starting, self-tapping screws including the option of partial or full cannulation. The screws include a cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess. The screws have a threaded distal end and a head including a torque driving recess. The head of the locking screw includes locking means, such as a variable locking mechanism, which could be a bushing that mates with the screw head so as to lock the screw relative to the plate at a desired angle, or could include external screw threads that mate with internal threads in the locking screw hole at a pre-selected angle, in this instance, the screw axis is perpendicular to the longitudinal axis of the plate. The screw used in the anti-rotation slot has a rounded rear shoulder (such as a hemisphere, or a torroid) which mates with the edges of the slot.

The implant is formed of a biocompatible material, and preferably a metal such as surgical grade stainless steel, titanium or a titanium alloy or a cobalt chromium alloy. Preferably, the plate portion has a thickness of between about 1.0 and about 2.5 millimeters, more preferably between about 1.5 and about 2 millimeters, and most preferably between about 1.5 and about 1.8 millimeters. The body portion of the implant has a curved cross-section having a diameter defining a total thickness of about 4 and 8 millimeters, or roughly four times the width of the plate portion of the implant.

In addition, the implant can include additional small through holes sized to receive a K-wire or other similar guide wire.

During the surgery the joints are first prepped which may include de-articulation between the bones to be fused and removal of any bone as part of the osteotomy, and as necessary, the plate is bent to contour to the bone surface. A pilot hole or preferably, an Eichhorn shaped recess may be drilled into the bone into which the implant will be inserted. The implant is inserted into the implant recess in the driver and secured by tightening the implant upward in the holder using the holder. The implant is tamped into the cancellous portion of the bone fragment optionally by tapping the implant driver with a one pound mallet as is necessary to insert the body of the implant. The implant should be driven until it is fully seated. Once the implant is sunk, a drill guide is mated to the driver, and a hole is drilled for the transverse screw. The implant can be held in position using k-wires or olive wires (thru the non-locking hole and into the bone). The plate portion is located such that all of the screws are aimed into the targeted bones and away from the joint, fracture, or bone interface. The olive wire is removed if used, and a pilot hole is drilled at the end of the plate that includes the first hole and this hole is pinned or screwed. A second pilot hole may be drilled for the transverse. The plate is viewed radiographically, and the soft tissues are closed in the usual manner.

This invention has been described in detail with reference to specific embodiments thereof, including the respective best modes for carrying out each embodiment. It shall be understood that these illustrations are by way of example and not by way of limitation.

What is claimed is:

1. An implant for an osteotomy of an associated long bone, comprising:
   a plate defining one or more through holes each being suitable for receiving a plate fastener; and
   a body having a first end and a second end joined by a curved surface with a through hole defined by the body that is suitably oriented so as to accept a body fastener that is oriented perpendicular to the body so as to lodge within an intramedullary canal of a bone to thereby preclude rotation (i) within the canal and (ii) about the osteotomy site, the first end being swaged and the second end extending into the plate so as to form an integral two member implant.

2. An implant according to claim 1, wherein the body further includes a through hole for a receiving a fastener.

3. An implant according to claim 2, wherein the implant further includes a fastener for the plate portion.

4. An implant according to claim 3, wherein the implant further includes a fastener for the body.

5. An implant according to claim 3, wherein the through hole in the body defines an angle for the fastener that is perpendicular to a long axis of the body.

6. An implant according to claim 5, wherein the first end is chamfered.

7. An implant according to claim 6, wherein the first end includes a counterbore.

8. An implant according to claim 1, wherein the plate includes two through holes each arranged so as to receive at least one fastener.

9. An implant according to claim 8, wherein the through holes are locking through holes and the fasteners are locking fasteners.

10. An implant according to claim 1, wherein the plate is a separate portion of the implant that is joined to the body in advance of a surgery.

11. An implant according to claim 1, wherein the plate is offset from a long axis of the body.

12. An implant according to claim 1, having at least two plate portions.

13. An implant according to claim 1, wherein the through hole in the plate is offset from a long axis.

14. An implant according to claim 1, wherein a bottom surface of the plate defines a longitudinal axis and includes a radius of curvature defined along the longitudinal axis.

15. An implant according to claim 14, wherein the radius of curvature is defined by a section of a cylinder.

16. An implant for an osteotomy comprising:
   a plate including at least one hole arranged and configured for receiving a fastener; and
   a body having a first end and a second end joined together by an exterior surface formed along a long axis, configured to lodge within an intramedullary canal of a long bone, the exterior surface including at least two of grooves arranged in parallel relation to one another so as to provide for inhibition of implant rotation within the long bone, the first end being swaged to facilitate insertion into the long bone and defining a threaded through hole adjacent to the swaged portion of the first end and configured to receive a threaded fastener, wherein the second end extends into the plate so as to form an integral two member implant.

17. An implant for use during an osteotomy comprising:
   a first portion configured to cooperate with a bone surface, the first portion defining at least one through hole; and
   a cannulated body having a first end and a second end joined by an exterior surface formed along a long axis, configured to lodge within an intramedullary canal of a bone, the exterior surface including at least two flanges that spiral around the body and are arranged in tapering, spaced circumferential relation to the cannulation so as to inhibit the implant from rotating within the bone, the first end being swaged to facilitate insertion into the bone with a threaded through hole defined adjacent to the swage and configured to receive a threaded fastener, and the second end extending into the first portion so as to form an integral two member implant.

* * * * *